United States Patent [19]
von Hollen

[11] Patent Number: 6,086,247
[45] Date of Patent: Jul. 11, 2000

[54] DIFFERENTIAL TEMPERATURE SENSOR DEVICE FOR USE IN THE DETECTION OF BREAST CANCER AND BREAST DISEASE

[76] Inventor: Dirk von Hollen, 16 Charles St., Clark, N.J. 07066

[21] Appl. No.: 09/018,765

[22] Filed: Feb. 5, 1998

[51] Int. Cl.⁷ ............ G01K 3/00; A61B 10/00; A61B 5/0492

[52] U.S. Cl. .......... 374/137; 374/162; 600/549; 600/391

[58] Field of Search ............ 374/14, 137, 162; 600/372, 382, 391, 392, 393, 395, 386, 474, 549

[56] References Cited

U.S. PATENT DOCUMENTS

| | | | |
|---|---|---|---|
| Re. 30,446 | 12/1980 | Meyers et al. | 128/736 |
| Re. 32,000 | 10/1985 | Sagi | 600/549 |
| 3,661,142 | 5/1972 | Flam | 600/549 |
| 3,830,224 | 8/1974 | Vanzetti et al. | 600/549 |
| 3,847,139 | 11/1974 | Flam | 600/549 |
| 3,960,138 | 6/1976 | Doss et al. | 600/549 |
| 4,055,166 | 10/1977 | Simpson | 600/549 |
| 4,064,872 | 12/1977 | Caplan | 600/549 |
| 4,135,497 | 1/1979 | Meyers et al. | 600/549 |
| 4,138,889 | 2/1979 | Fraschini | 73/356 |
| 4,190,058 | 2/1980 | Sagi | 600/549 |
| 4,232,684 | 11/1980 | Chervitz | 600/549 |
| 4,403,653 | 9/1983 | Davidson | 165/170 |
| 4,418,697 | 12/1983 | Tama | 600/382 |
| 4,428,382 | 1/1984 | Walsall et al. | 600/549 |
| 4,524,778 | 6/1985 | Brown, Jr. | 600/549 |
| 4,524,779 | 6/1985 | Brown, Jr. | 600/549 |
| 4,624,264 | 11/1986 | Sagi | 600/549 |
| 4,651,749 | 3/1987 | Sagi | 600/549 |
| 4,682,605 | 7/1987 | Hoffman | 600/549 |
| 4,747,413 | 5/1988 | Bloch | 600/549 |
| 4,952,033 | 8/1990 | Davis | 350/351 |
| 5,058,999 | 10/1991 | Davis | 600/549 |
| 5,124,819 | 6/1992 | Davis | 359/53 |
| 5,301,681 | 4/1994 | DeBan et al. | 600/549 |
| 5,401,100 | 3/1995 | Thackston | 374/208 |
| 5,772,591 | 6/1998 | Cram | 600/382 |

FOREIGN PATENT DOCUMENTS 1130157  8/1982  Canada .

OTHER PUBLICATIONS

Brueschke, et al., Relative Densitometric Analysis of Thermograms, Annnals New York Academy of Sciences, vol. 121:80–89, (Oct. 9, 1964).

Gershen–Cohen, et al., Modalities in Breast Cancer Detection: Xerography, Cancer, vol. 24( No. 6);1226–1230, (Dec. 1969).

Gershen–Cohen, et al., Advances in Thermography and Mammography, Annals New York Academy of Science, vol.121:283–300, (Oct. 9, 1964).

*Primary Examiner*—Randy W. Gibson
*Attorney, Agent, or Firm*—Cooper & Dunham LLP

[57] ABSTRACT

A differential temperature sensor device is provided for detecting differential temperatures in a human breast. A pad having a contoured design is covered with an adhesive layer having differing release forces on its two sides to insure sustained contact between the breast and temperature sensors and to ease removal after use. Temperature sensors are arranged in a useful pattern and covered with a silicon lidding which is removed prior to use. The device is especially useful for the detection of breast cancer and breast disease.

41 Claims, 4 Drawing Sheets

DIFFERENTIAL TEMPERATURE SENSOR DEVICE FOR USE IN THE DETECTION OF BREAST CANCER AND BREAST DISEASE

BACKGROUND OF INVENTION

The present invention relates to a differential temperature sensor device used to detect and visually display surface temperatures on a body within a predetermined range. The device is particularly useful in the early detection of cancerous tumors and disease in the human breast.

There are many known devices and methods for the detection of cancerous breast tumors and breast disease. Procedures for the detection of breast tumors and breast disease presently include physical examination, mammography, xerography, and thermography.

For a historical discussion of the various methods of detecting breast cancer and disease see the article by Gershen-Cohen et al entitled "Modalities In Breast Cancer Detection Xerography", in Cancer (December, 1969), pp. 1226–1230; see also "Advances In Thermography and Mammography", by Gershen-Cohen et al, Annals New York Academy of Sciences (1964), pp. 283–300; and "Relative Densiometric Analysis of Thermograms", by Brueschke et al., Annals New York Academy of Sciences (1964), pp. 82–89.

In the 1950's, it was discovered that the surface temperature of skin in the area of a malignant tumor exhibits a higher temperature than that expected where no disease is present. Thus, by measuring skin surface temperatures, it became possible to screen for the existence of abnormal body activity such as cancerous tumor growth. This knowledge was eventually applied to the detection of malignant breast tumors and breast disease. Consequently, much effort has been expended in exploring different approaches to measuring skin temperature in the breast region. The goals in this area have been to provide a non-invasive, inexpensive, self-contained, comfortable, reliable device for performing such screening, while at the same time giving the patient both a sense of privacy and control over when and how the screening process is performed.

Many different devices and methods have been directed towards breast cancer and breast disease detection through temperature measurement. For example, U.S. Pat. No. 4,428,382 to Walsall et al. discloses a probe responsive to thermal radiation which is passed over skin to measure its temperature and identify the presence of abnormal tissue. A thermoresponsive screen used in conjunction with a photographic system is described by U.S. Pat. No. 4,524,779 to Brown, Jr. In U.S. Pat. No. 4,055,166 to Simpson et al., a brassiere is disclosed in which transistorized temperature sensors are disposed in order to provide skin temperature measurements for the purpose of locating cancerous growths. A similar device based on thermistors used in conjunction with a neural network is disclosed in the U.S. patent to Deban et al. (No. 5,301,681). However, each of these types of approaches typically failed to meet one or more of the goals described above.

With the development of liquid crystals and methods of forming temperature responsive chemical substrates, contact thermography became a practical method of breast cancer and breast disease screening. Devices employing contact thermography were developed which could sense and display temperature changes through indicators which changed colors, either permanently or temporarily, when placed in direct physical contact with a skin surface reflecting a temperature at or near the point of contact. This technology enabled a contemporaneous temperature measurement of both of a woman's breasts to be made and compared since dissimilar temperatures in the same regions of opposing breasts could indicate the presence of malignancy or other abnormality. An anomalous temperature comparison reading would at least indicate the need to seek more detailed examination of the physical regions in question.

The accuracy of such devices is contingent upon sustained, uniform contact for an adequate time period between the breast and thermographic sensors. As women's breasts are a variety of different shapes and sizes, and women wear a variety of different styles and sizes of brassieres, the passive placement of sensors in general contact with the breast, such as in a brassiere, cannot insure sufficient, uniform, sustained contact between breast and sensor to yield a reliable temperature profile. A portion of the breast may not come into contact with a sensor, or may move away from the sensor before the examination time passes. The body of prior art comprises many breast temperature sensor devices. However, none of them adequately solved the problems of inaccuracy, discomfort and difficulty of use of breast temperature sensor devices.

U.S. Pat. No. 3,847,139 to Flam discloses a substrate of body-conforming material carrying a temperature responsive coating viewable against the substrate background for displaying a temperature indicative pattern when the structure is worn over the breasts. However, the Flam device was a cumbersome one, designed to be worn between the neck and waist of a woman and required an intricate fastener.

Flam U.S. Pat. No. 3,661,142 discloses a temperature-sensing patch which is attached on one side to a flexible backing web and on the other side to a plurality of discrete temperature-sensitive indicators. Each indicator comprises a layer of encapsulated cholesteric liquid crystals, which have the property of changing color with changes in temperature. However, this device provided a limited area of measurement. U.S. Pat. No. 3,830,224 to Vanzetti et al. was directed to the placement of temperature sensors in a brassiere. However, the area of measurement provided by this device also was limited. Further, the device required a predetermined brassiere shape which resulted either in certain areas of the breast not contacting a desired liquid crystal or the breasts themselves being deformed into an unnatural shape by the brassiere thereby damaging the reliability of the resulting temperature reading.

Uniformly close contact between skin and sensors was provided by Meyers et al. (U.S. Pat. No. Re. 30,466) in which temperature responsive film containing temperature sensitive liquid crystals was wrapped across the breast area and the air between the breasts and the film was mechanically evacuated. But this invention required specialized, expensive extra equipment for its implementation. U.S. Pat. No. 4,524,778 to Brown Jr. et al. disclosed an approach in which hot areas indicated by a thermographic scanning band overlaying the breast area were traced by hand onto an overlying web and the highest temperature at each site of unusual activity indicated by the thermogram was separately measured in situ by means of a hand-held liquid crystal activated thermometer so a record of temperature readings over time can be obtained. This device required multiple measurement steps and depended on readings from single temperature indicators spaced out over a relatively large area.

Another temperature-responsive device for detecting the presence of breast cancer is described by James et al in U.S. Pat. No. 3,960,138. This device is retained in thermal contact with thermistors in each cup of a brassiere, which are connected to create a differential temperature integrator circuit, whereby any difference in mean temperatures between the two breasts may be monitored over a period of time.

A series of patents to Sagi (U.S. Pat. Nos. 4,190,058 and Re. 32,000; U.S. Pat. No. 4,624,264 and U.S. Pat. No. 4,651,749) generally described disc-shaped cancer detection patches for aid in early detection of breast cancer based on thermography. The patches comprise radially arranged rows of temperature responsive indicators deposited on a plurality of pie-shaped, heat-conductive web segments made of aluminum foil. The patches are placed into the breast-receiving cups of a brassiere, in contact with the breasts, then visually examined for temperature differentials to determine possible abnormality of breast tissue.

The backing of the Sagi patents, webbing composed of solid metallic foil, especially when mounted on a support surface, does not always conform well to complex three-dimensional shapes such as human breasts. In addition, although the diagnostic device of Sagi provides the ability to cover a much broader area of breast surface than the prior art, it is not self-contained and must be manufactured in a multiplicity of sizes to accommodate different breast shapes and sizes. Then, if the brassiere into which the segments are inserted does not itself fit perfectly, uniform skin contact with the diagnostic device is still not achieved. Moreover, in order to compensate for differences in brassiere design, insertion of the segments into the brassiere could result in overlapping segments causing the indicators of some segments to become hidden and, therefore, useless.

One way to insure sustained contact between breast and sensor is to attach a sensor directly to the breast itself, preferably using an adhesive. However, application of adhesive directly to the sensor can interfere with the transmission of heat to the sensor, resulting in inaccurate readings. Further, large surface-area contact between breast and adhesive also can irritate breast skin and can make removal of the sensor from delicate breast skin difficult.

SUMMARY OF INVENTION

It is an object of this invention to provide a differential temperature sensor device which provides increased ease of use, comfort and accuracy over prior art devices.

Another object of the invention is to provide a differential temperature sensor device for use in the early detection of breast cancer whereby temperature sensors are placed in direct contact with the breast.

Another object of the invention is to provide a differential temperature sensor device for use in the early detection of breast cancer and breast disease which provides direct contact between the breast and sensor components without the need for applying adhesive directly to the sensors.

Another object of the invention is to provide a differential temperature sensor device for use in the early detection of breast cancer and breast disease which accommodates varying breast sizes and shapes.

The invention is an improvement over the prior art, and provides a foam breast sensor pad having on one face a two-sided adhesive layer which secures the sensors to the pad and provides perimeter adhesive around the sensors for good contact with a breast to be examined. This construction is found to have advantages over placing adhesive directly on the sensors, including reduction of interference with the transmission of heat to the sensors, and reduction in skin irritation and reactions caused by large body area contact with adhesive. The invention provides an adhesive layer having an aggressive adhesive on one side to create a strong bond between the adhesive layer and a foam pad, while supplying a more gentle adhesive between skin and pad, avoiding difficulty of removal of the pads from patients. The differential release force created by the two different adhesives allows the pad to be easily removed from a patient, without causing the adhesive layer to separate from the pad. An alternative improved pad design also is provided.

The foregoing and other objects of this invention will be more clearly comprehended from the following detailed description of the invention and the accompanying drawings.

DETAILED DESCRIPTION OF INVENTION

The present invention contemplates a differential temperature sensor device, useful in the early detection of breast cancer and breast disease, with improved contact between sensor and breast, which decreases the incidence of incorrect readings in breast thermography and which is comfortable and easy to use. The device includes a double-sided adhesive layer, having a front and back with differential release forces. A pad having a contoured design is covered with the adhesive layer. Sensors are arranged in a useful pattern on the adhesive and held in place by the adhesive. The entire pad is then applied to the breast.

It is well known that the average difference in surface temperature of the breasts is larger for persons with a malignant tumor or certain types of breast disease in one breast than those having normal (non-malignant) breasts. Moreover, the temperature difference in malignant mammary tumors is usually more than 1° C. (1.8° F.), and is invariably more than 0.6° C. (1.08° F.). Also, while the temperature of normal breasts tends to fluctuate, the temperature of a malignant or diseased breast remains relatively constant, at a higher temperature, than the temperature of the normal breast.

This invention provides an improved method and device for monitoring such differences between malignant and non-malignant breasts, while providing improved accuracy, comfort and ease of use.

Figure 1:
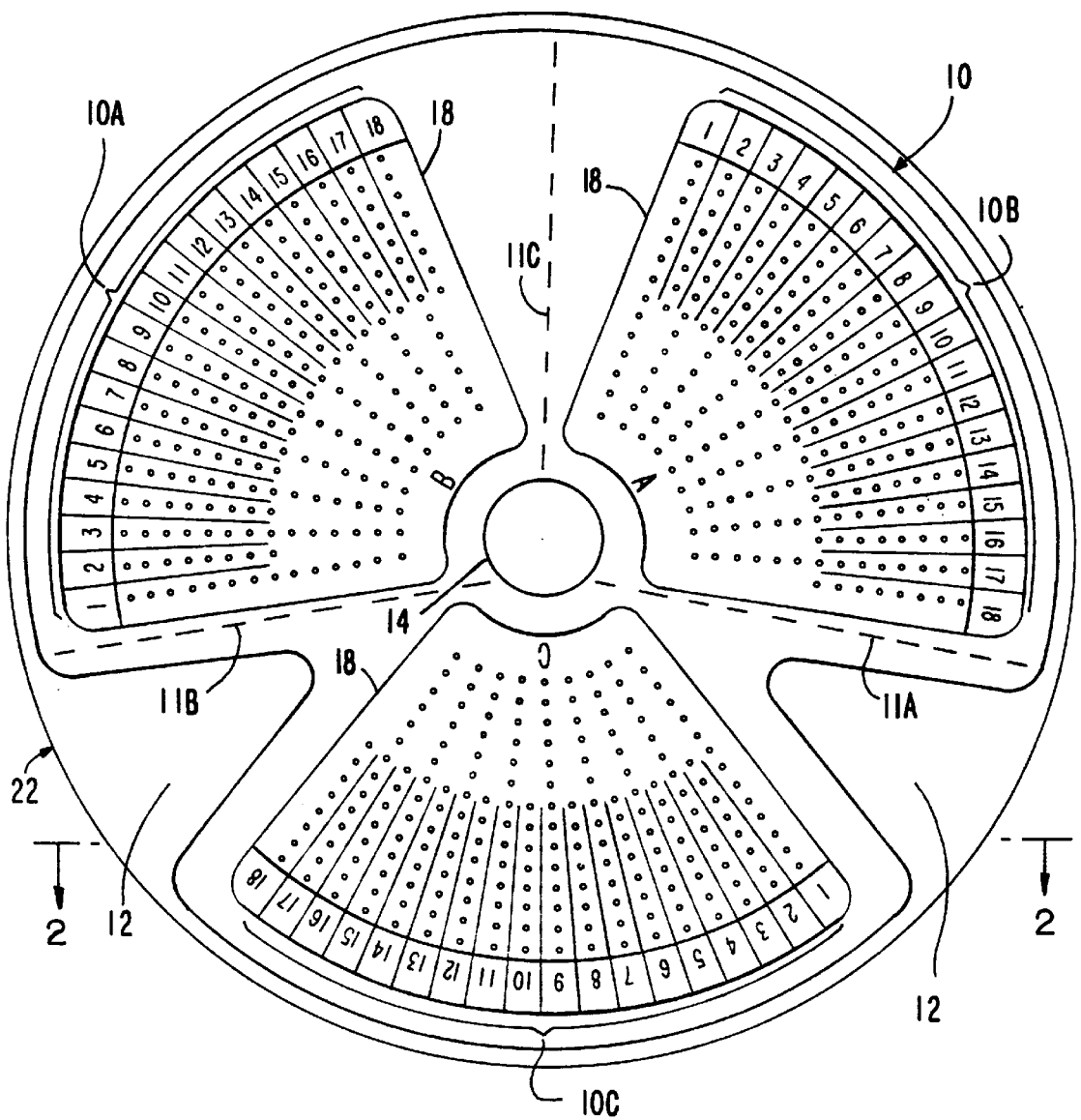
FIG. 1 is a plan view of the device of the present invention.

The device comprises pad 10. In a preferred embodiment, as seen in FIG. 1 of the drawings, pad 10 is disk-shaped with two triangular cut-outs 12, creating a mushroom-like shaped pad. Pad 10 has nipple hole 14 in its center. Pad 10 may be made of any flexible or rigid material. Preferable results are obtained with a thin flexible material with plastic properties such as polyurethane or polyester open or closed cell material, such as is available from Polymer Technologies of Delaware, U.S.A. It has been found that polyurethane or polyester open or closed cell material is superior to fiberous materials, which tend to come apart when a pad is pulled from a breast. Pad 10 may also be contructed of suitable textile products such as woven, knitted, braided or nonwoven fabric. Pad 10 may be made in various convenient shapes and in sizes ranging from about 5 inches to about 9 inches in diameter to accommodate a wide variety of breast sizes. Various other cut-outs can be added to pad 10 to alter the general shape as shown in FIG. 1, as will be disclosed below.

Figure 2:
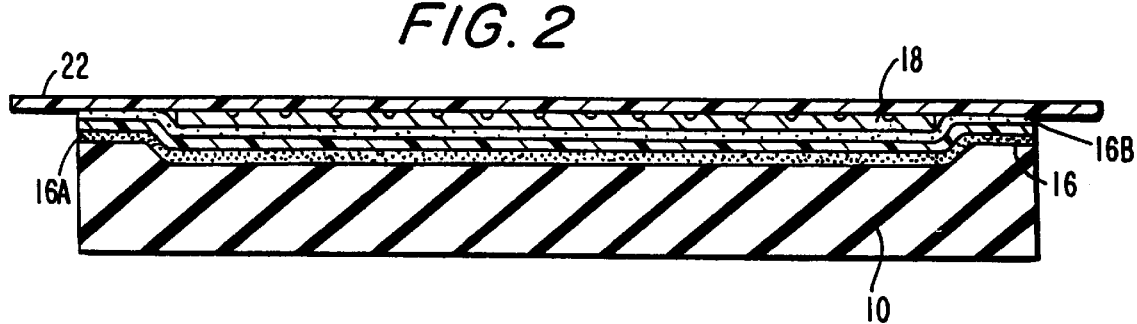
FIG. 2 is a sectional view taken along the line 2—2 in FIG. 1.

As shown in FIG. 2, pad 10 is covered on one face with a two-sided adhesive layer 16 which matches the shape of pad 10. Adhesive layer 16 may be constructed from a variety of adhesives and substrates, such as rubber, pressure-sensitive materials or acrylic. In one embodiment, such adhesive is applied to both sides of a polyester film or web. Adhesive layer 16 also can be formed by spraying an adhesive directly on pad 10, laying a liner on the adhesive and spraying an additional layer of adhesive on the liner, creating a double-sided adhesive. Side 16A of adhesive layer 16 is coated with an adhesive which is relatively more aggressive than that of side 16B. Where sprayed adhesive is used, a relatively more aggressive adhesive is sprayed directly on pad 10, a liner is then placed on the adhesive, and a less aggressive adhesive is sprayed on the side of the liner which does not contact pad 10. Regardless of the embodiment, a differential release force between the respective sides of adhesive layer 16 is an important aspect of the present invention. Even a minute difference in release force has been found to be effective. This release force differential allows pad 10 to be removed from the skin of a patient without causing the separation of adhesive layer 16 from pad 10. A preferable double-sided adhesive film, useful as adhesive layer 16, is manufactured by CSI-Scapatapes of Connecticut, U.S.A.

The less aggressive adhesive of adhesive layer 16 is sufficient to hold sensors 18 to pad 10. This feature simplifies manufacture, as the same adhesive used to secure sensors 18 to pad 10 is used to secure pad 10 to the breast. At the same time, the more aggressive adhesive keeps sensors 18 attached to pad 10, while the less aggressive adhesive releasably attaches cad 10 to the body.

In a preferred embodiment, as shown in FIG. 1, pad 10 is comprised of three substantially equal triangular shaped segments 10A, 10B and 10C. For ease of reference, the triangular segments 10A, 10B and 10C are delineated by broken lines 11A, 11B and 11C. Sensors 18 are placed on surface 16B of adhesive layer 16, in segments 10A, 10B and 10C of pad 10. This arrangement of sensors 18 allows good coverage of the three discrete sections of the breast to be examined: the inner section, which faces the other breast, the outer section, which faces away from the other breast, and the lower, or underside of the breast. The preferred arrangement also allows the underlying adhesive layer to be exposed in areas around each sensor and around the perimeter of pad 10. Exposure of the less aggressive adhesive around a portion of the sensors has been found desirable.

Figure 3:
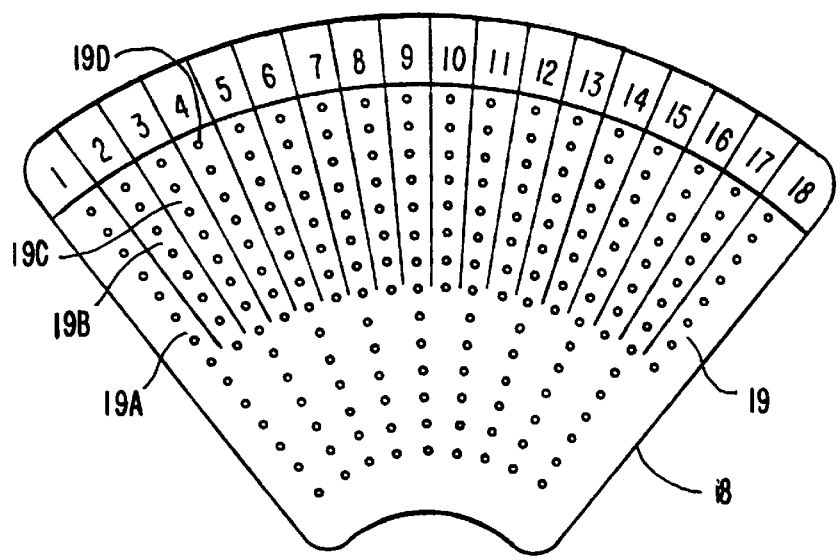
FIG. 3 is a plan view of a sensor used in the device of the present invention.

There are several generally available temperature sensors available which are suitable for use in connection with the present invention, including those of the type generally disclosed in the Sagi patents discussed above (U.S. Pat. No. 4,190,058 and U.S. Pat. No. Re. 32,000; U.S. Pat. No. 4,624,264 and U.S. Pat. No. 4,651,749). These sensors generally employ compounds which change color in the presence of heat. Such sensors are available from Humascan, Inc. of New Jersey, U.S.A. Sensor 18 of this general type is shown in FIG. 3 and comprises alternating rows of eight and fourteen rows of indicators 19. The alternating rows 19A to 19N correspond to respective temperature ranges of 89° F. to 93° F. and 89° F. to 96° F., in 0.5° F. gradations.

The number of indicators as well as the temperature range and temperature gradations may vary. However, for breast cancer detection, eight to fourteen indicators per quadrant covering the aforementioned temperature range, in 0.5° F. gradations, have been found satisfactory. Other suitable arrays and ranges may also be used.

Other temperature sensors, including electrical or electronic sensors, also can be used, with suitable results.

In production of the device, sheets of material for the construction of pad 10 first can be covered with an adhesive layer 16, such as a double-sided adhesive film or tape. Pad 10 and adhesive layer 16 then can be cut from the pad material. In a preferred embodiment, referring to FIG. 1, circular discs forming pad 10, and triangular shapes 12 and nipple hole 14 can then be cut from the pad material and adhesive layer simultaneously, providing an exact match in shape between pad 10 and adhesive layer 16. Of course, any desired pad shape may be chosen.

Sensors 18 then are applied to adhesive layer 16 in the arrangement shown in FIG. 1, or any other useful arrangement, and the entire sensor bearing surface of pad 10 is covered with a lidding 22 of polyester-type material which is coated with silicone on the side contacting the sensors. Lidding 22 is sized to completely cover pad 10 and is disk-shaped. Lidding 22 protects adhesive layer 16 until use and allows for proper inspection of color indicating dots prior to use. Lidding 22 is removed at the time of application.

Figure 4:
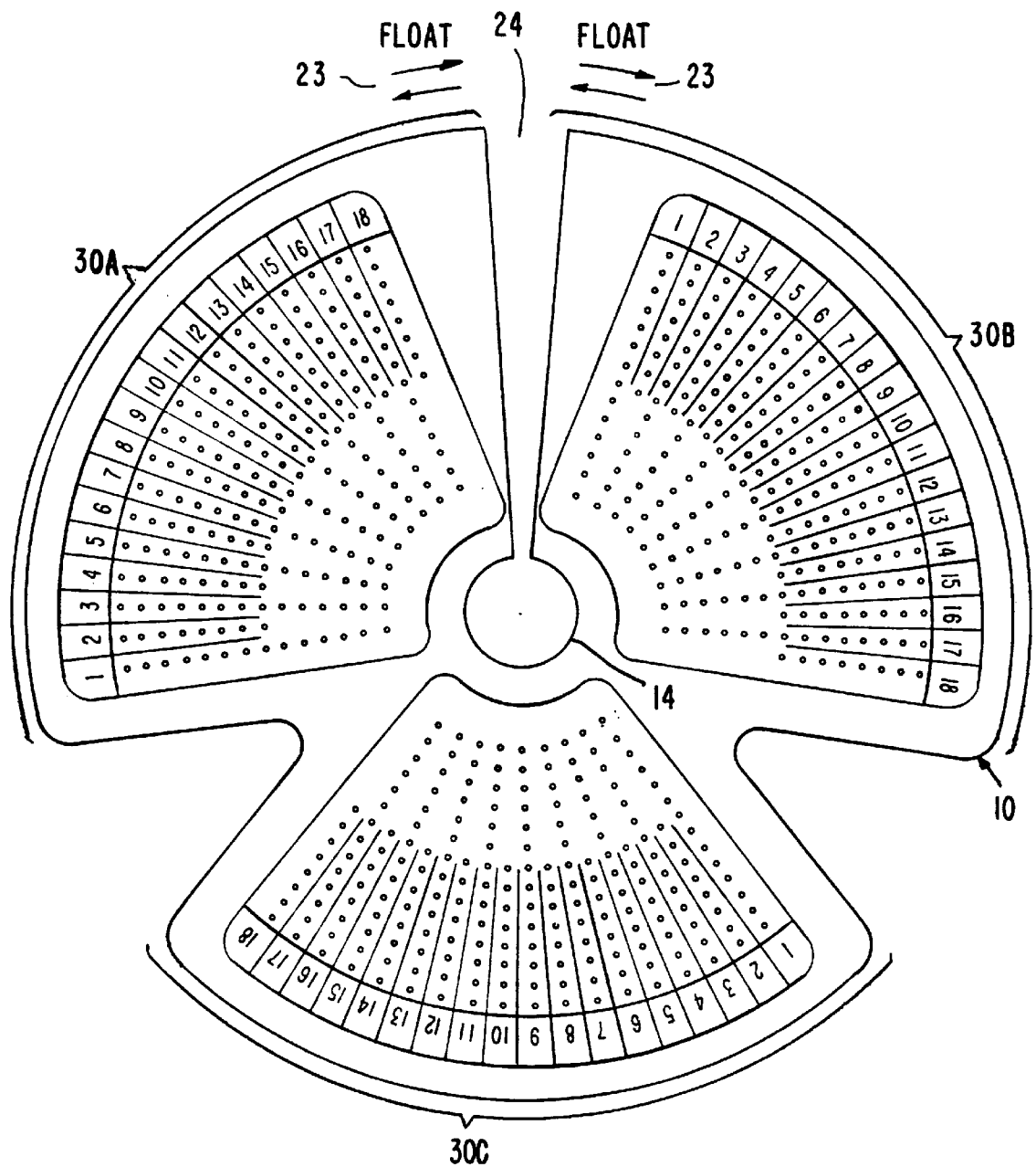
FIG. 4 is a plan view of the device of the present invention illustrating a different embodiment of the invention.
Figure 5:
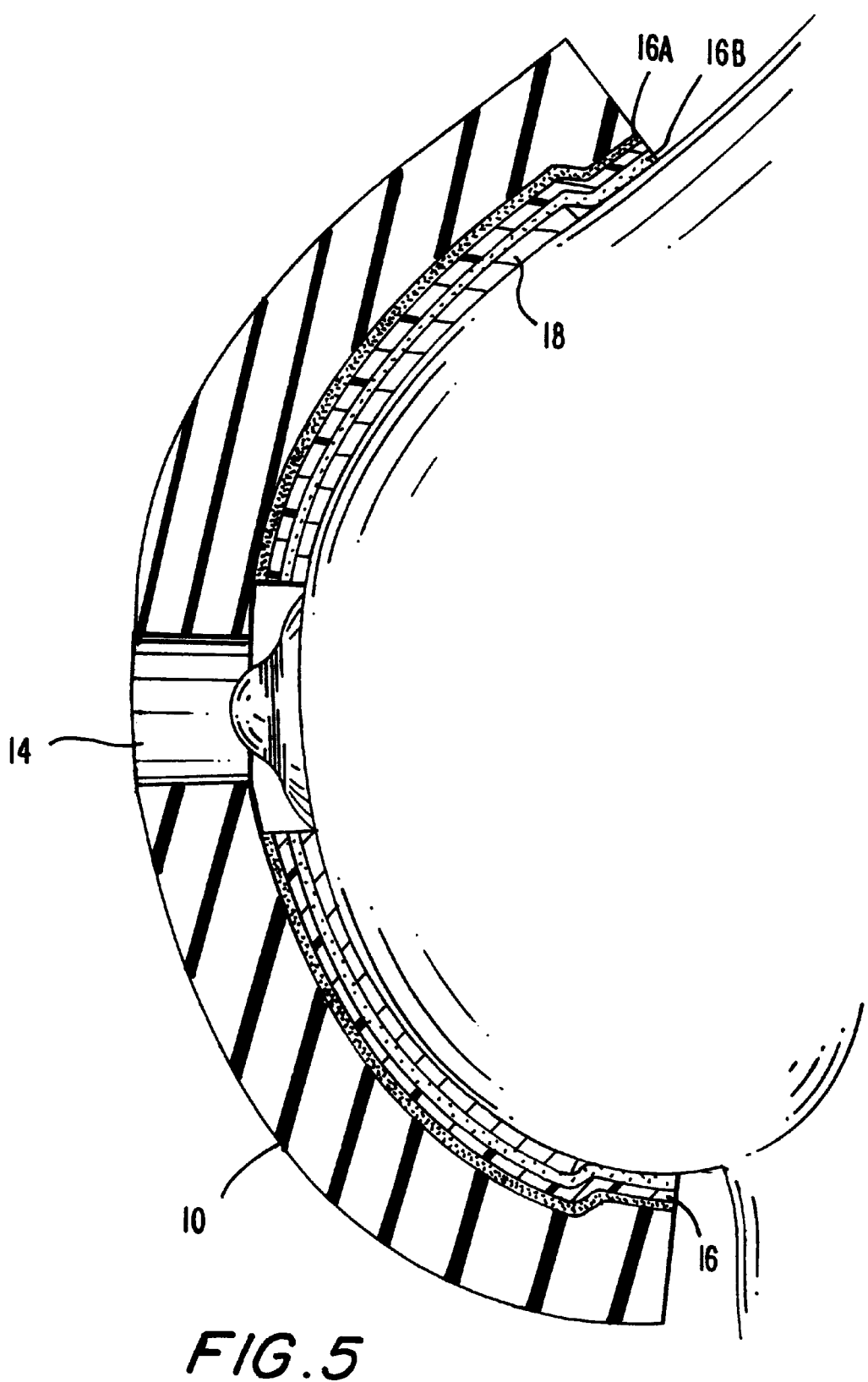
FIG. 5 is a sectional view of the device of the present invention as applied to a human breast.

A further modification to the preferred design of pad 10 is shown in FIG. 4. Slot 24 is cut into pad 10 between the two adjacent top segments, creating three distinct pie-shaped sensor-containing segments 30A, 30B and 30C. Slot 24 extends from the perimeter of pad 10 to nipple hole 14. This modification provides for positive segment location to the inner contour of the breast, due to float 23 created by slot 24 and the elasticity of pad 10.

In use, a practitioner, such as a physician or nurse, applies the device. The patient is asked to be seated in an upright position, wearing a brassiere that fully covers the breasts. The front of the brassiere cup covering the left breast is lowered to expose the left breast. The practitioner selects a pad 10 labeled "left breast" and removes lidding 22 from pad 10, exposing sensors 18 and portions of adhesive layer 16 and taking care to avoid touching sensors 18. Nipple hole 14 is placed over the nipple, enabling the nipple to protrude from nipple hole 14. Lifting the breast, if necessary, and beginning below the breast, the practitioner places sensor 18 in segment 10A against the breast, and presses segment 10A against the breast from the crease under the breast, up toward the nipple, then proceeds to press segments 10B and 10C against the breast. The practitioner then holds pad 10 in place, and checks to insure that all sensors 18 are in contact with breast skin. The patient is then asked to stretch the brassiere cup and strap forward and over pad 10, securing it in place as the practitioner's hand is withdrawn. The procedure is repeated for the right breast. The application of pads 10 to both breasts should be performed in less than two minutes to insure accurate results.

Once in place, a light-weight garment is worn over the brassiere and the patient is asked to remain seated, quietly, for fifteen minutes. The practitioner then removes pad 10 from the left breast, making certain the adhesive on pad 10 does not contact or fold over on itself. The removal procedure is repeated for the right breast. Both pads 10 are placed sensor side up on a table or counter, and results are recorded within two minutes of removal, beginning with the left breast pad.

Results are then recorded. The practitioner or an assistant, working with one section at a time, records the highest column number (1–18 as shown on FIG. 3) in which three or more temperature sensitive dots have turned from blue to pink. Columns with only one or two pink dots are disregarded. The count for each segment of the left breast pad is compared with the count for the same segment on the right breast pad. The absolute difference (+ or − is disregarded) is recorded. The results are then evaluated. An absolute difference of 3 or less for a segment is considered within the range of normal temperature variability. A difference of 4 or more is considered outside the range of normal temperature variability and additional investigation is indicated.

Infrequently, a patient's evaluation may indicate that the breast temperature is either below the tested range (below 90° F. no dots turn pink) or above the tested range (above 98.5° F. all dots turn pink). For this small population a difference of three columns or less may not be applicable. However, a difference of four columns or more can be used.

As the pads of the invention are non-invasive and non-irritating, fresh pads may be used as frequently as desired. Used pads are not reused.

Various alternative constructions can be employed without departing from the spirit or scope of the invention.

I claim:

1. A differential temperature sensor device comprising:
   (a) a pad having two opposite surfaces;
   (b) an adhesive layer positioned on one surface of said pad and also having opposite surfaces, the bottom surface of said adhesive layer contacting said pad and being coated with an adhesive which is relatively aggressive and the upper surface of said adhesive layer facing away from the said pad and being coated with an adhesive which is relatively less aggressive; and
   (c) an array of spaced-apart temperature sensors arranged on the upper surface of said adhesive layer such that a portion of said pad and said adhesive layer protrude around a portion of said temperature sensors.

2. A differential temperature sensor device of claim 1 wherein said pad is flexible.

3. A differential temperature sensor device of claim 1 wherein said pad is made of foam.

4. A differential temperature sensor device as in claim 1 wherein said temperature sensors are pie-shaped.

5. A differential temperature sensor device as in claim 1 wherein said pad is disk-shaped.

6. A differential temperature sensor device as in claim 1 wherein said pad is made of polyurethane.

7. A differential temperature sensor device as in claim 1 wherein said pad is made of polyester open cell material.

8. A differential temperature sensor device as in claim 1 wherein said pad is made of polyester closed cell material.

9. A differential temperature sensor device as in claim 1 wherein said pad is made of a textile material.

10. A differential temperature sensor device as in claim 9 wherein said pad is made of woven fabric.

11. A differential temperature sensor device as in claim 9 wherein said pad is made of braided fabric.

12. A differential temperature sensor device as in claim 9 wherein said pad is made of knitted fabric.

13. A differential temperature sensor device as in claim 9 wherein said pad is made of non-woven fabric.

14. A differential temperature sensor device as in claim 1 wherein said pad is covered on the sensor-bearing side by a lidding of silicon-coated plastic.

15. A differential temperature sensor device as in claim 1 having at least two temperature sensors arranged thereon.

16. A differential temperature sensor device as in claim 1 wherein said temperature sensors are electronic.

17. A differential temperature sensor device as in claim 1 wherein said temperature sensors are electrical.

18. A differential temperature sensor device as in claim 1 wherein the adhesive coating on said adhesive layer is a rubber adhesive.

19. A differential temperature sensor device as in claim 1 wherein the adhesive coating on said adhesive layer is an acrylic adhesive.

20. A differential temperature sensor device as in claim 1 wherein the adhesive coating on said adhesive layer is a pressure sensitive adhesive.

21. A differential temperature sensor device for detecting temperature variations in a human body, comprising:
   (a) a pad having opposite surfaces;
   (b) an adhesive layer on one surface of said pad, having a shape substantially that of said pad, and having opposite, adhesive coated surfaces, wherein a bottom surface of said adhesive layer contacts said pad and is coated with a relatively aggressive adhesive and a top surface of said adhesive layer is coated with a less aggressive adhesive; and
   (c) an array of spaced-apart temperature sensors arranged on the top surface of said adhesive layer such that a portion of said pad and said adhesive layer protrudes around a portion of said temperature sensors,
whereby when the device is placed on the human body, said sensors are adjacent the body and the less aggressive adhesive coating releasably secures both the sensors and the pad to the body.

22. A differential temperature sensor device as in claim 21 wherein said pad is disk-shaped and has two removed portions in a first one-half of said pad, such that a segment of the first one-half of said pad between the removed portions is centrally located in relation to the second one-half of said pad and is about one-half the size of the second one-half of said pad.

23. A differential temperature sensor device as in claim 22 further having a nipple hole and a slot in said pad extending from the perimeter of said pad to said nipple hole.

24. A differential temperature sensor device as in claim 21 wherein said temperature sensors are pie-shaped.

25. A differential temperature sensor device as in claim 21 wherein said temperature sensors have a plurality of temperature sensitive indicators thereon.

26. A differential temperature sensor device as in claim 21 wherein said pad is covered on the sensor-bearing side by a lidding of silicon-coated plastic.

27. A differential temperature sensor device as in claim 21 wherein said pad is made of polyurethane.

28. A differential temperature sensor device as in claim 21 wherein said pad is made of polyester open cell material.

29. A differential temperature sensor device as in claim 21 wherein said pad is made of polyester closed cell material.

30. A differential temperature sensor device as in claim 21 wherein said pad is made of a textile material.

31. A differential temperature sensor device as in claim 30 wherein said pad is made of woven fabric.

32. A differential temperature sensor device as in claim 30 wherein said pad is made of braided fabric.

33. A differential temperature sensor device as in claim 30 wherein said pad is made of knitted fabric.

34. A differential temperature sensor device as in claim 30 wherein said pad is made of non-woven fabric.

35. A differential temperature sensor device as in claim 21 wherein said adhesive layer comprises a rubber adhesive.

36. A differential temperature sensor device as in claim 21 wherein said adhesive layer comprises an acrylic adhesive.

37. A differential temperature sensor device as in claim 21 wherein said adhesive layer comprises a pressure sensitive adhesive.

38. A differential temperature sensor device as in claim 21 wherein said pad is covered on the sensor-bearing side by a lidding of silicon-coated plastic.

39. A differential temperature sensor device as in claim 21 having at least two temperature sensors arranged thereon.

40. A differential temperature sensor device as in claim 21 wherein said temperature sensors are electronic.

41. A differential temperature sensor device as in claim 21 wherein said temperature sensors are electrical.

* * * * *